United States Patent [19]

Budai et al.

[11] Patent Number: 5,254,547
[45] Date of Patent: Oct. 19, 1993

[54] THIOACID AMIDE DERIVATIVES AND FODDER COMPOSITIONS CONTAINING THE SAME

[75] Inventors: Zoltán Budai; Tibor Mezei; Klára Reiter née Esses; Lajos Fekete; Károly Magyar; Attila Nagy; László Puskás, all of Budapest, Hungary

[73] Assignee: EGIS Gyogyszergyar, Budapest, Hungary

[21] Appl. No.: 802,236

[22] Filed: Dec. 4, 1991

[30] Foreign Application Priority Data

Dec. 22, 1990 [HU] Hungary ............................... 8447/90

[51] Int. Cl.⁵ ........................................... A61K 31/535
[52] U.S. Cl. ................................. 514/237.5; 426/807
[58] Field of Search .................... 544/161; 426/2, 807, 426/623, 635; 514/237.5

[56] References Cited

U.S. PATENT DOCUMENTS 4,489,074 12/1984 Brown et al. ....................... 424/246

FOREIGN PATENT DOCUMENTS

0080296A1 6/1983 European Pat. Off. .
2102246 2/1972 Fed. Rep. of Germany .
56-12316 2/1981 Japan .

OTHER PUBLICATIONS

Formenti, Arch of Toxical. Suppl. 1980 Y 284-7.

*Primary Examiner*—Robert Gerstl
*Attorney, Agent, or Firm*—Beveridge, DeGrandi Weilacher & Young

[57] ABSTRACT

The invention relates to new thioacid amide derivatives, a process for the preparation thereof, compositions, particularly feed additives, premixes and ready-for-use fodders, comprising the same, further to a method for increasing weight gain and improving fodder utilization of domestic animals.

The new thioacid amide derivatives of the general formula (I), wherein

R represents hydrogen, $C_{1-18}$ alkyl, $C_{2-6}$ alkenyl or $C_{2-6}$ alkynyl and $R^1$ stands for hydrogen, halogen or methoxy, with the provisos that a) at least one of R and $R^1$ is other than hydrogen;
b) if R represents ethyl, $R^1$ is other than hydrogen; and
c) if R stands for methyl, $R^1$ is other than hydrogen or methoxy, exhibit useful weight-gain increasing and fodder-utilization improving effects and can be used in animal husbandry, particularly in pig.

5 Claims, No Drawings

THIOACID AMIDE DERIVATIVES AND FODDER COMPOSITIONS CONTAINING THE SAME

This invention relates to new thioacid amide derivatives, a process for the preparation thereof, feed additives, premixes and ready-for-use fodders comprising the same, further to a method for increasing weight gain and improving fodder utilization of domestic animals.

It is known that 4-(3'-methoxy-4'-hydroxythio-benzoyl)-morpholine possesses choleretic activity (Martin Negwer: "Organic-chemical drugs and their synonyms", Akademie-Verlag; Berlin, 1987).

It is also known that 4-(3',4',5'-trimethoxythio-benzoyl)-morpholine exerts ulcus secretion inhibiting properties [Farina, C., Pinza, M., Gomba, A. and Pifferi, G.: Eur. J. Med. Chem. 14, 27–31 (1979)).

According to an aspect of the present invention there are provided new thioacid amides of the general formula (I)

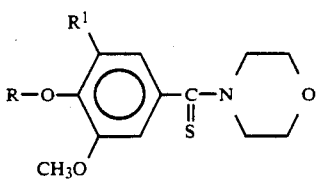

wherein
R represents hydrogen, $C_{1-18}$ alkyl, $C_{2-6}$ alkenyl or $C_{2-6}$ alkynyl and
$R^1$ stands for hydrogen, halogen or methoxy, with the provisos that
a) at least one of R and $R^1$ is other than hydrogen;
b) if R represents ethyl, $R^1$ is other than hydrogen; and
c) if R stands for methyl, $R^1$ is other than hydrogen or methoxy.

The term "$C_{1-18}$ alkyl" used throughout the specification relates to straight or branched chained saturated aliphatic groups having the given number of carbon atoms (e.g. methyl, ethyl, n-propyl, isopropyl, n-butyl, n-hexyl, n-dodecyl, n-hexadecyl etc.). As "$C_{2-6}$ alkenyl" groups straight or branched chained alkenyl groups are mentioned (e.g. vinyl, allyl, propenyl etc.). The term "$C_{2-6}$ alkynyl" relates to straight or branched chained alkynyl groups (e.g. propynyl). The term "halogen" encompasses all the four halogen atoms, such as fluorine, chlorine, bromine and iodine.

A particularly advantageous representative of the compounds of the general formula (I) is the following derivative:
4-(4'-hexyloxy-3-methoxyphenyl)-thioxomethylmorpholine.

According to a further aspect of the present invention there is provided a process for the preparation of the compounds of the general formula (I), wherein R and $R^1$ are as stated above, which comprises
a) reacting an aldehyde of the general formula (II)

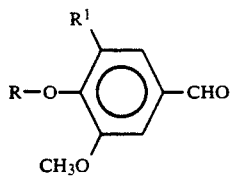

wherein R and $R^1$ are as stated above, with morpholine and sulfur; or
b) reacting a carboxylic acid of the general formula (III),

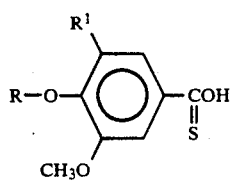

wherein R and $R^1$ are as stated above, or a reactive derivative thereof with morpholine or
c) reacting a morpholide of the general formula (IV),

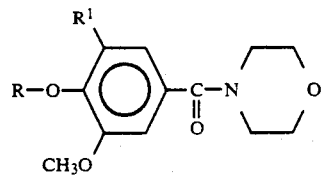

wherein R and $R^1$ are as stated above, with a thionating agent;
and, if desired, reacting a compound of the general formula (I), wherein R stands for hydrogen, obtained according to any of process variants a)–c) with a compound of the formula $R^2$-Hlg, wherein Hlg represents halogen and $R^2$ stands for $C_{1-18}$ alkyl, $C_{2-6}$ alkenyl or $C_{2-6}$ alkynyl.

According to variant a) of the process of the invention an aldehyde of the general formula (II) is reacted with morpholine and sulfur. The molar ratio of the aldehyde, morpholine and sulfur is generally 1:2:1, but one of them may also be applied in a slight excess.

The reaction is performed at elevated temperatures, preferably without using any solvent, in melt. The reaction temperature may vary between 40° C. and 160° C., and it is preferably about 120° C.

The time of the reaction depends on the temperature and may vary between wide ranges. If the reaction is carried out at a relatively low temperature (e.g. at 60° C.), the time of reaction may be as long as 50–60 hours. At a relatively high temperature (140° C.) the reaction may be accomplished within 0.5–0.8 hour. At 120° C. the optimum reaction time is 1 hour.

The compounds of the general formula (I) can be isolated from the reaction mixture by known methods after adding a solvent (e.g. by crystallization after cooling or by evaporation).

According to variant b) of the process of the invention an acid derivative of the general formula (III) is reacted, preferably after having been activated, with morpholine.

The activation of the acid of the general formula (III) can be carried out in different ways. It is preferable to convert it into the corresponding halide with a halogenating agent such as phosphorus pentachloride, phosphorus trichloride oxide, thionyl chloride etc. The halide thus obtained is then reacted with morpholine in the presence of an acid-binding agent. The reaction is preferably carried out in a solvent inert toward the reactants. As solvent aromatic hydrocarbons, e.g. toluene, benzene, xylene etc., ethers such as tetrahydrofurane, diisopropyl ether etc. can be used. The morpholine used as reagent may serve as acid-binding agent, but organic or inorganic bases can also be applied for the same purpose. As organic base e.g. piperazine, triethylamine, ammonia etc., as inorganic base alkali hydroxides, carbonates or hydrogen carbonates may be used. As reactive acid derivatives anhydrides, mixed anhydrides (e.g. chloroformates) or esters (e.g. alkyl esters) may also be used.

According to variant c) of the process according to the invention a morpholide derivative of the general formula (IV) is reacted with a thionating agent, preferably with diphosphorus pentasulfide, in a solvent inert toward the reactants, preferably in pyridine, at an elevated temperature, preferably between 40° C. and 160° C., at the boiling point of the solvent applied.

The compound of the general formula (I) thus obtained, wherein R represents hydrogen, can optionally be alkylated, alkenylated or alkynylated. The reaction is preferably carried out with the corresponding chloride or bromide by methods known per se, in the presence of a basic condensing agent. For this purpose alkali carbonates (e.g. sodium or potassium carbonate), alkali hydrogen carbonates or alkali alcoholates can be used. The reaction is preferably performed under heating. It is particularly preferable to keep the reaction mixture boiling while using a reflux condenser.

The aldehydes of the general formula (II) used as starting compounds are known from the literature [i. Prakt. Chem. 318, (5) 785-94 (1976)]. The carboxylic acid derivatives of the general formula (III) can be prepared as described in U.S. patent specification Ser. No. 1,855,454. The morpholides of the general formula (IV) can be prepared according to Example 4.

The compounds of the general formula (I) possess useful weight-gain increasing properties on domestic animals, particularly on pig, which is accompanied by a valuable fodder-utilization improving effect.

The weight-gain increasing effect of the compounds of the general formula (I) is shown by the following test:

Pigs are used as test animals. Each animal group consists of 6 pigs and each test with 6 pigs is repeated 3 times. The fodder contains 50 mg/kg of the test compund of the general formula (I). The animals are fed under identical conditions and all the animal groups receive the same amount of fodder having the same composition. The animals of the control group are fed with the same fodder but without test compound of the formula (I). The results are summarized in Table I.

TABLE I

| Test compound | Average daily weight gain | | Weight of fodder producing 1 kg of weight gain | |
|---|---|---|---|---|
| | g/day | % | kg | % |
| Example 1 | 323.5 | 111.7 | 2.05 | 89.5 |

TABLE I-continued

| Test compound | Average daily weight gain | | Weight of fodder producing 1 kg of weight gain | |
|---|---|---|---|---|
| | g/day | % | kg | % |
| Control | 289.5 | 100.0 | 2.29 | 100.0 |

From the above data it can be seen that the weight gain of the animals fed with a fodder containing a compound of the invention is significantly higher than that of the pigs of the control group. At the same time the same weight gain can be achieved with a considerably smaller amount of fodder when a compound of the general formula (I) is incorporated to the animal feed. This is a proof of an improved fodder utilization.

A very important advantage of the compounds of the general formula (I) is that they are discharged from the animal organism more readily than the known weight-gain increasing compounds and they do not show any mutagenic effect. This fact constitutes a significant advantage when used in animal husbandry.

The toxicity of the compounds of the general formula (I) on domestic animals is so low that the compounds are practically nontoxic.

According to a further aspect of the invention there are provided compositions, particularly fodder additives, premixes and ready-for-use fodders, comprising as active ingredient an amount of 0.0001% to 85% by weight of a compound of the general formula (I), wherein R and $R^1$ are as stated above, in admixture with inert solid or liquid carriers or diluents.

According to a further aspect of the invention there is provided a process for the preparation of fodder additives, premixes and ready-for-use fodders, which comprises admixing a compound of the general formula (I), wherein R and $R^1$ are as stated above, with suitable edible solid or liquid carriers or diluents and optionally with additives generally used in the production of fodder additives and fodders.

As carrier any substance of vegetable or animal origin applicable in the feeding of animals can be used. For this purpose e.g. wheat, barley, bran, maize, soybean, oats, rye, alfalfa can be used in appropriate forms (grits, groats, meal etc.), furthermore fish meal, meat meal, bone meal or mixtures thereof can be used as well. One may advantageously use a fiber-free green plant fodder concentrate with high protein content.

As additives e.g. silicic acid, antioxidants, starch, dicalcium phosphate, calcium carbonate, sorbic acid etc. can be used.

As wetting agent e.g. nontoxic oils, preferably soybean oil, maize oil or mineral oil can be applied. Various alkylene glycols can also be used as wetting agent. The starch used may be e.g. wheat, maize or potato starch.

The active agent content of the compositions may vary within wide ranges. The fodder additives and concentrates may contain about 5 to 80% by weight, preferably about 10 to 80% by weight, of the active ingredient of the general formula (I). The active ingredient content of the animal fodders ready for use may be about 0.0001 to 0.04% by weight, preferably about 0.001 to 0.01% by weight. The fodder additives and concentrates may contain usual vitamins (e.g. vitamin A, $B_1$, $B_2$, $B_3$, $B_6$, $B_{12}$, E, K) and trace elements (e.g. Mn, Fe, Zn, Cu, I), too.

The fodder additives and concentrates are diluted with suitable fodder components or are incorporated into suitable animal feeds to provide animal feeds ready for use.

The fodder additives, premixes and ready-for-use fodders according to the present invention can be used for increasing the weight gain and improving feed utilization of various domestic animals such as pigs, lambs, cattle, poultry, particularly pigs.

According to a further aspect of the present invention there is provided a method for improving weight gain and fodder utilization of animals, which comprises feeding the animals with a fodder or feed additive of the invention.

According to a still further aspect of the present invention there is provided the use of the compounds of the general formula (I) for the increase of weight gain and improvement of feed utilization of domestic animals.

Further details of the present invention are to be found in the following Examples of non-limiting character. The melting points appearing in the Examples are not corrected.

EXAMPLE 1

4-(4'-Hexyloxy-3-methoxyphonyl)-thioxomethylmorpholine 261.3 g (3.0 mole) of morpholine, 48.0 g (1.6 mole) of powdered sulfur and 354.5 g (1.5 mole) of 4-n-hexyloxy-3-methoxybenzaldehyde are allowed to react at the boiling point of the mixture for 2 hours. The product is crystallized from ethanol.

Yield: 486.5 g (96.1%) of yellow lamellated crystals
M.p.: 105°–107° C.
Analysis for the formula $C_{18}H_{27}NO_3S$ (337.5):
calculated: C %=64.06  H %=8.06  N %=4.17  S %=9.50
found: C %=64.28  H %=8.14  N %=4.20  S %=9.44
UV: $\lambda_{max}$=283 nm ($\epsilon$=15599)

EXAMPLE 2

4-[4'-(1-Propenyloxy)-3'-methoxyphenyl]-thioxonothylaorpholine 174.2 g (2.0 mole) of morpholine, 35.3 g (1.1 mole) of powdered sulfur and 192.1 g (1.0 mole) of 4-(1-propenyloxy-3-methoxy)-benzaldehyde are reacted at the boiling point of the reaction mixture for 4 hours. Then ethanol is added to it and the desired product is isolated by crystallization.

Yield: 273.1 g (93.1 of yellow powdery crystals
M.p.: 188°–190° C.
Analysis for the formula $C_{15}H_{19}NO_3S$ (293.3):
calculated: C %=61.40  H %=6.52  N %=4.77  S %=10.92
found: C %=61.63  H %=6.97  N %=4.80  S %=10.95
UV: $\lambda_{max}$=286 nm ($\epsilon$=15410)

EXAMPLE 3

4-[4'(1-Propynyloxy)-3'-methoxyphenyl-thiozomethylmorpholine 63.35 g (0.25 mol) of 4-(4'-hydroxy-3'-methoxyphenyl)-thioxomethylmorpholine are reacted with 20.1 g (0.27 mole) of 3-chloro-l-propyne in dimethylformamide, in the presence of 27.5 (0.2 mole) of potassium carbonate at the boiling point of the reaction mixture for 4 hours. The desired compound is then precipitated with water and filtered.

Yield: 63.0 g (86.5%) of yellow powder
M.p.: 111°–113° C.
Analysis for the formula $C_{15}H_{17}NO_3S$ (291.4):
calculated: C %=61.83  H %=5.88  N %=4.81  S %=11.01
found: C %=61.94  H %=5.99  N %=4.82  S %=10.94
UV: $\lambda_{max}$=282 nm ($\epsilon$=14101)

The starting compound is prepared as follows:

104.5 g (1.5 mole) of morpholine, 32.0 g (1.0 mole) of powdered sulfur and 152.2 g (1.0 mole) of 4-hydroxy-3-methoxybenzaldehyde are reacted at the boiling point of the mixture (115° C.) for 4 hours. The product is crystallized from ethanol.

Yield: 226.8 g (89.5%) of yellow crystals
M.p.: 167°–168° C.
Analysis for the formula $C_{12}H_{15}NO_3S$ (253.4):
calculated: C %=56.87  H %=5.97  N %=5.56  S %=12.65
found: C %=57.02  H %=6.05  N %=5.49  S %=12.66
UV: $\lambda_{max}$=281 nm ($\epsilon$=15442)

EXAMPLE 4

4-(4'-Dodecyloxy-3'-methoxyphenyl)-thioxomothylmorpholine

One proceeds according to Example 3 except that instead of 3-chloro-1-propyne 67.3 g (0.27 mole) of 1dodecylbromide are used. The desired compound is precipitated with water and filtered.

Yield: 264.9 g (83.8%) of yellow powder
M.p.: 104°–106° C.
calculated: C %=68.36  H %=9.32  N %=3.32  S %=7.61
found: C %=68.40  H %=9.45  N %=3.34  S %=7.61
UV: $\lambda_{max}$=283 nm ($\epsilon$=15517)

EXAMPLE 5

4-(4'-Butoxy-3'-methoxyphenyl)-thioxomethylmorpholine

One proceeds according to Example 3 except that instead of 3-chloro-1-propyne 37.0 9 (0.27 mole) of 1-bromobutane are used.

Yield: 87.9 g (94.7%) of yellow lamellated crystals
M.p.: 113°–115° C.
Analysis for the formula $C_{16}H_{23}NO_3S$ (309.6):
calculated: C %=62.10  H %=7.49  N %=4.52  S %=10.34
found: C %=62.31  H %=7.52  N %=4.61  S %=10.39
UV: $\lambda_{max}$=284 nm ($\epsilon$=14195)

EXAMPLE 6

4-[3'-Bromo-4'-(1-propynyloxy)-5'-methoxyphonyl]-thioxomethylaorpholine

One proceeds according to Example 1 except that instead of 354.5 g (1.5 mole) 4-n-hexyloxy-3-methoxybenzaldehyde 403.8 g (1.5 mole) 3-bromo-4-(1-propynyloxy)-5-methoxybenzaldehyde are used.

Yield: 509.4 g (91.7%) of yellow crystals
M.p.: 137°–139° C.
Analysis for the formula $C_{15}H_{16}BrNO_3S$ (370.4):
calculated: C %=48.64  H %=4.35  N %=3.78  Br %=21.58  S %=8.66 found: C %=48.59 H %=4.43 N %=3.87 Br %=21.63 S %=8.80

UV: $\lambda_{max}$=283 nm ($\epsilon$=11976)

EXAMPLE 7

4-(3'-Bromo-4'-hydroxy-5'-methoxyphenyl)-thioxomethylaorpholine

One proceeds according to Example 1 except that instead of 354.5 g (1.5 mole) of 4-n-hexyloxy-3-methoxy-benzaldehyde 346.65 g (1.5 mole) of 3-bromo-4-hydroxy-5-methoxybenzaldehyde are used.

Yield: 282.8 g (85.1%) of yellow powder

Mp.: 197°–199° C.

Analysis for the formula $C_{12}H_{14}BrNO_3S$ (332.3):

calculated: C %=43.37 H %=4.24 Br %=24.04 N %=4.23 S %=9.64 found: C %=43.22 H %=4.39 Br %=23.97 N %=4.36 S %=9.87

UV: $\lambda_{max}$=284 nm ($\epsilon$=14877)

EXAMPLE 8

4-(3'-Bromo-4'-hexyloxy-5'-methoxythiobenzoyl)-morpholine

One proceeds according to Example 1 except that instead of 354.5 g (1.5 mole) of 4-hexyloxy-3-methoxybenzaldehyde 472.8 g of 3-bromoe-4n-hexyloxy-5-methoxybenzaldehyde are used.

Yield: 196.5 g (94.4%) of yellow crystals

M.p.: 83°–85° C.

Analysis for the formula $C_{18}H_{26}BrnO_3S$ (416.4):

calculated: C %=51.92 H %=6.29 Br %=19.19 N %=3.36 S %=7.69 found: C %=52.10 H %=6.35 Br %=19.19 N %=3.40 S %=7.74

UV: $\lambda_{max}$=284 nm ($\epsilon$=12796)

EXAMPLE 9

A premix for supplementing pig fodder is prepared with the following composition:

| Components | Amounts |
| --- | --- |
| Vitamin A | 3,000,000 NE |
| Vitamin $D_3$ | 600,000 NE |
| Vitamin E | 4,000 NE |
| Vitamin $K_3$ | 400 mg |
| Vitamin $B_1$ | 600 mg |
| Vitamin $B_2$ | 800 mg |
| Vitamin $B_3$ | 2,000 mg |
| Vitamin $B_6$ | 800 mg |
| Vitamin $B_{12}$ | 10 mg |
| Niacine | 4,000 mg |
| Choline chloride | 60,000 mg |
| Active agent according Example 1 | 10,000 mg |
| Butylhydroxytoluene (antioxidant) | 30,000 mg |
| Flavouring substances | 8,000 mg |
| Sodium saccharate | 30,000 mg |
| Trace elements: | |
| Mn | 8,000 mg |
| Fe | 30,000 mg |
| Zn | 20,000 mg |
| Cu | 6,000 mg |
| I | 1,000 mg |
| Twice-ground bran ad | 1,000 g |

This premix of vitamins and trace elements is admixed with the basal fodder in a concentration of 0.5 kg per 100 kg.

EXAMPLE 10

A premix for supplementing piglet fodder is prepared with the following composition:

| Components | Amounts |
| --- | --- |
| Vitamin A | 1,200,000 NE |
| Vitamin $D_3$ | 300,000 NE |
| Vitamin E | 2,000 NE |
| Vitamin $B_2$ | 600 mg |
| Vitamin $B_3$ | 2,000 mg |
| Vitamin $B_{12}$ | 5 mg |
| Niacine | 3,000 mg |
| Choline chloride | 40,000 mg |
| Active agent according Example 1 | 10,000 mg |
| Butylhydroxytoluene (antioxidant) | 30,000 mg |
| Trace elements: | |
| Mn | 6,000 mg |
| Fe | 10,000 mg |
| Zn | 15,000 mg |
| Cu | 30,000 mg |
| I | 100 mg |
| Twice-ground bran ad | 1,000 g |

This premix of vitamins and trace elements is admixed with the basal fodder in a concentration of 0.5 kg/100 kg.

EXAMPLE 11

0.5 kg of premix as described in Example 9 is admixed with a basal fodder to yield a total weight of 100.0 kg with the following composition:

| Components | Amounts |
| --- | --- |
| Maize | 37.6 kg |
| Barley | 25.4 kg |
| Wheat | 6.0 kg |
| Oats | 5.0 kg |
| Soybean | 13.0 kg |
| Fish meal | 6.0 kg |
| Bran | 2.4 kg |
| Fat powder | 1.5 kg |
| Premix of minerals | 1.0 kg |
| Lime (fodder quality) | 1.0 kg |
| Sodium chloride (fodder quality) | 0.5 kg |
| Biolysine | 0.1 kg |
| Premix according to Example 9 | 0.5 kg |
| Total weight: | 100.0 kg |

The active agent content of the resulting pig fodder is 0.005% by weight.

The composition of the premix of minerals is as follows:

| Components | Amounts, % by mass |
| --- | --- |
| Dicalcium phosphate | 55.0 |
| Monocalcium phosphate | 40.0 |
| Calcium carbonate | 5.0 |

EXAMPLE 12

0.5 kg of a premix as described in Example 10 is admixed with a basal fodder to yield a total weight of 100.0 kg with the following composition:

| Components | Amounts |
| --- | --- |
| Maize | 25.0 kg |
| Wheat | 34.0 kg |
| Extracted soybean | 18.0 kg |

| Components | Amounts |
| --- | --- |
| Milk powder | 9.9 kg |
| Fish meal | 4.0 kg |
| Yeast (fodder quality) | 2.0 kg |
| Fat powder | 3.4 kg |
| Premix of minerals according to Example 11 | 1.8 kg |
| Lime (fodder quality) | 1.0 kg |
| Sodium chloride (fodder quality) | 0.4 kg |
| Premix according to Example 11 | 0.5 kg |
| Total weight: | 100.0 kg |

The active agent content of the resulting piglet fodder is 0.005% by weight.

EXAMPLE 13

400 kg of a pre-ground soybean meal are filled into a mixer, 3.1 kg of soybean oil are added understirring, and the mixture is stirred until the solids get coated with oil. Thereafter 9.1 kg of an active agent according to Example 4 are added and the mixture is stirred until a homogeneous blend is obtained. Finally 9.0 kg of soybean oil are added and the mixture is homogenized again.

EXAMPLE 14

0.5 kg of an active agent according to Example 3 are added to 40 kg of corn meal under stirring, and simultaneously propylene glycol is sprayed into the mixture. Thereafter 1.4 kg of dicalcium phosphate are added and the mixture is homogenized.

EXAMPLE 15

10 kg of alfalfa meal and 15 kg of a fiber-free green plant fodder concentrate with high protein content are stirred for 20 hours, thereafter spraying of 1 kg of maize oil into the mixture is started with an even speed so that spraying is continued during the introduction of the following additional components: 2.5 kg of an active agent according to Example 1, 10 kg of maize starch, 0.3 kg of silicon dioxide, 0.6 kg of ascorbic acid and 9 kg of maize starch. The mixture thus obtained is stirred for additional 5 minutes.

EXAMPLE 16

One proceeds as described in Example 13 with the difference that 1,4-butylene glycol is applied as wetting agent instead of soybean oil.

EXAMPLE 17

A) 3.5 kg of potato starch are admixed with 2.9 kg of an active agent according to Example 8. 0.05 kg of mineral oil are sprayed into the mixture, thereafter 0.2 kg of sorbic acid, 0.4 kg of silicon dioxide and 0.1 kg of calcium propionate are added, and the mixture is stirred for additional 2 minutes.

B) 4.2 kg of fish meal are admixed with 22 kg of rye bran, 0.6 kg of mineral oil are sprayed into the mixture, thereafter 4 kg of a mixture prepared according to point A), 10 kg of maize meal, 4 kg of a mixture prepared according to point A) and 9 kg of maize meal are introduced under stirring. Finally 0.6 kg of mineral oil are sprayed into the mixture.

EXAMPLE 18

100 kg of wheat bran, 10 kg of an active agent according to Example 5, 2.5 kg of calcium carbonate, 0.15 kg of α-tocopherol and 0.4 kg of calcium propionate are homogenized with 4 kg of propylene glycol.

EXAMPLE 19

10 kg of soybean meal and 0.6 kg of an active agent according to Example 6 are homogenized with 2.5 kg of 1,4-butylene glycol.

EXAMPLE 20

50 kg of soybean meal, 6 kg of an active agent according to Example 7, 0.5 kg of silicon dioxide, 1.6 kg of soybean oil and 0.2 kg of calcium propionate are homogenized.

What we claim is:

1. A composition for use in animal feed to increase the weight gain of the animal comprising, as active ingredient, 4-(4'-hexyloxy-3-methoxyphenyl)-thioxomethyl-morpholine in admixture with suitable inert solid or liquid carriers or diluents.

2. The composition as defined in claim 1, wherein said animal feed is animal fodder.

3. The composition as defined in claim 1, wherein said solid carriers are selected from the group consisting of wheat, barley, bran, maize, soybean, oats, rye, alfalfa, fish meal, meat meal, bone meal and mixtures thereof.

4. The composition as defined in claim 1, wherein said animal is a domestic animal.

5. The composition as defined in claim 4, wherein said domestic animal is selected from the group consisting of pig, lamb, cattle and poultry.

* * * * *